(12) United States Patent
Miret Carceller et al.

(10) Patent No.: US 11,206,859 B2
(45) Date of Patent: Dec. 28, 2021

(54) FOOD-GRADE COATED PARTICLES CONTAINING POLYCARBOXYLIC ACIDS

(71) Applicant: VENTA DE ESPECIALIDADES QUÍMICAS, S.A., Terrassa (ES)

(72) Inventors: Jordi Miret Carceller, Barcelona (ES); Carles Lozano Perez, Montgat (ES); Roger Segret Pons, Barcelona (ES)

(73) Assignee: VENTA DE ESPECIALIDADES QUÍMICAS, S.A., Terrassa (ES)

( * ) Notice: Subject to any disclaimer, the term of this patent is extended or adjusted under 35 U.S.C. 154(b) by 64 days.

(21) Appl. No.: 16/770,499

(22) PCT Filed: Dec. 13, 2018

(86) PCT No.: PCT/EP2018/084845
§ 371 (c)(1),
(2) Date: Jun. 5, 2020

(87) PCT Pub. No.: WO2019/115733
PCT Pub. Date: Jun. 20, 2019

(65) Prior Publication Data
US 2021/0219585 A1    Jul. 22, 2021

(30) Foreign Application Priority Data

Dec. 14, 2017 (EP) .................... 17382850

(51) Int. Cl.
| | | |
|---|---|---|
| *A23L 27/00* | (2016.01) |
| *A23K 20/158* | (2016.01) |
| *A23K 40/30* | (2016.01) |
| *A23K 20/105* | (2016.01) |
| *A23P 10/35* | (2016.01) |
| *A23G 3/40* | (2006.01) |
| *A23G 3/54* | (2006.01) |
| *A61K 8/02* | (2006.01) |
| *A61K 8/362* | (2006.01) |
| *A61K 8/60* | (2006.01) |
| *A23G 3/34* | (2006.01) |
| *A23G 3/36* | (2006.01) |
| *A23G 4/06* | (2006.01) |
| *A23G 4/20* | (2006.01) |
| *A23P 10/30* | (2016.01) |

(52) U.S. Cl.
CPC ............... *A23L 27/72* (2016.08); *A23G 3/40* (2013.01); *A23G 3/54* (2013.01); *A23K 20/105* (2016.05); *A23K 20/158* (2016.05); *A23K 40/30* (2016.05); *A23P 10/35* (2016.08); *A61K 8/0245* (2013.01); *A61K 8/362* (2013.01); *A61K 8/60* (2013.01); *A23V 2002/00* (2013.01); *A61K 2800/10* (2013.01); *A61K 2800/652* (2013.01)

(58) Field of Classification Search
CPC ....... A23L 27/72; A23K 20/158; A23K 40/30; A23K 20/105; A23P 10/35; A23P 10/30; A23G 3/40; A23G 3/54; A23G 3/343; A23G 3/36; A23G 4/062; A23G 4/20; A61K 8/0245; A61K 8/362; A61K 8/60; A61K 2800/10; A61K 2800/652; A23V 2002/00

See application file for complete search history.

(56) References Cited

U.S. PATENT DOCUMENTS

| 8,431,171 B2 | 4/2013 | Notebaart et al. |
| 2014/0199439 A1 | 7/2014 | Sarama et al. |

FOREIGN PATENT DOCUMENTS

| EP | 3127434 | 2/2017 |
| WO | WO 2002/080706 A2 | 10/2002 |
| WO | WO 2007/124093 A2 | 11/2007 |
| WO | WO 2008/006878 A1 | 1/2008 |

*Primary Examiner* — Trevor Love
(74) *Attorney, Agent, or Firm* — Squire Patton Boggs (US) LLP

(57) ABSTRACT

It relates to a food-grade coated particle comprising: a) a core that comprises a ($C_4$-$C_{12}$)polycarboxylic acid; and b) a coating that comprises: (i) an alkali metal salt of a ($C_4$-$C_{12}$) polycarboxylic acid wherein at least one carboxylic group of the ($C_4$-$C_{12}$)polycarboxylic acid is in the acid form, and at least one carboxylic group of the ($C_4$-$C_{12}$)polycarboxylic acid is in the salt form, and (ii) a film-forming agent; wherein the weight ratio between (i) and (ii) is from 20:80 to 40:60. It also relates to processes for the preparation of these food-grade coated particles, to their use as food additives, as well as to foodstuffs comprising them.

20 Claims, No Drawings

FOOD-GRADE COATED PARTICLES CONTAINING POLYCARBOXYLIC ACIDS

CROSS-REFERENCE TO RELATED APPLICATIONS

This application is a national-stage filing under 37 USC 371(c) of International Application No. PCT/EP2018/084845, file Dec. 13, 2018, which claims priority to, and the benefit of, European Patent Application EP17382850.0, filed Dec. 14, 2017, the entire contents of each of which are herein incorporated by reference in their entirety for all purposes.

This application claims the benefit of European Patent Application EP17382850.0 filed on Dec. 14, 2017.

TECHNICAL FIELD

The present invention relates to food-grade coated particles containing polycarboxylic acids. It also relates to a process for their preparation, to their use as food additive and to foodstuffs comprising them.

BACKGROUND ART

Polycarboxylic acids such as citric acid, malic acid or tartaric acid are commonly used additives in food products. One of the fields where these acids are mostly used is the confectionery industry including for example hard and soft candies and chewing-gums, where a fast release of said polycarboxylic acids is desired to produce an intense acidic taste sensation.

These hygroscopic acids are deliquescent, so they absorb water from the atmosphere. Moreover, these polycarboxylic acids, due to their intrinsic acidic nature can cause detrimental interactions in some food matrix. For instance, when applied as acidulent for soft jelly candies, they can promote sugar inversion reactions, altering the stability of the jelly.

As a consequence, different encapsulation technologies have been developed to protect these acids from the environment, thus overcoming the above-mentioned drawbacks of environmental moisture intake and undesirable migrations in foodstuffs.

In the past few years, protective coatings from fat origin have been extensively used to encapsulate these acidulants. The hydrophobic nature of the fat coatings provides the needed protective barrier from hygroscopicity. However, these coatings result in a too slow release of the active in water media which is detrimental to the taste sensation.

The European patent EP3127434 describes the use of monoglycerides, diglycerides and their combinations as coatings for food ingredients (e.g. organic acids). Generally, glycerides result in more elastic coatings than the typically used hydrogenated fats (palm, sunflower); they are tasteless and allow a good moisture protection. However, glycerides can be too soft for certain applications such e.g. the manufacture of candies since they show sticky behaviour during production and make the preparation of the particles difficult. Furthermore, particles coated with glycerides in the amount needed to guarantee a good moisture barrier for the encapsulated acid show a slow release in water, which has a negative effect on the taste.

In another approach, the U.S. Pat. No. 8,431,171 describes the use of salts (e.g. sodium monohydrogen malate) as protective coatings of active ingredients (food grade acids). However, since layers made of these salts have limited film-forming properties, high amounts of salts (at least 50 wt % with respect to the total weight of the particle) have to be used to create a thicker layer that effectively protects the acid in the core from hygroscopicity. As a consequence, the acid taste of the encapsulated organics acids is modified by the amount of salt used in the coating process. Additionally, the inventors observed also moderate cracking of the coating layer containing the high amount of salt when the particles were subjected to a friction process. Thus, the particles disclosed in U.S. Pat. No. 8,431,171 are brittle and, consequently, difficult to manipulate.

Therefore, from what is known in the art there is a need to develop a coating layer which not only protects the said acids from the environment but also permits a fast release of the active and overcomes the problems of the prior art.

SUMMARY OF INVENTION

The inventors have found that when food-grade acids are encapsulated with a combined coating layer containing a mixture of a film-forming agent (such as e.g. a monoglyceride), and an alkali metal salt of a $(C_4-C_{12})$polycarboxylic acid in a specific ratio, the amount of coating with respect to the total amount of the particle can be reduced and the resulting particles show an increased hardness when compared to the particles of the prior art. This improved hardness, on the one hand, prevents brittleness and cracking, and, on the other hand, facilitates manipulation during production and use.

Furthermore, as demonstrated in the examples below, the hydrophobic nature of the combined coating layer is capable of forming an encapsulating film around the acid in the core that acts as a moisture barrier providing good hygroscopic protection, so that the particles of the invention show good stability during its shelf-life.

Besides, the particles of the invention allow a fast release of the encapsulated acid and have the further advantage that the taste of the acid is not modified. This can be of special interest in applications such as hard/soft candies and chewing-gums, where the fast release of the food-grade acids should provide a strong and prolonged sour taste sensation.

Therefore, an aspect of the present invention relates to a food-grade coated particle comprising:
a) a core that comprises a $(C_4-C_{12})$polycarboxylic acid; and
b) a coating that comprises:
(i) an alkali metal salt of a $(C_4-C_{12})$polycarboxylic acid wherein at least one carboxylic group of the $(C_4-C_{12})$polycarboxylic acid is in the acid form, and at least one carboxylic group of the $(C_4-C_{12})$polycarboxylic acid is in the salt form, and
(ii) a film-forming agent; wherein
the weight ratio between (i) and (ii) is from 20:80 to 40:60.

The invention further relates to simple and fast processes for the preparation of the above particles. Thus, a second aspect of the invention relates to a process for the preparation of the food-grade coated particles as defined above, which comprises:
a) dispersing or dissolving an alkali metal salt of a $(C_4-C_{12})$polycarboxylic acid (i) as defined above, in a film-forming agent (ii) at a suitable temperature; wherein the weight ratio between (i) and (ii) is from 20:80 to 40:60; and
b) spraying the dispersion or solution of step a) onto a $(C_4-C_{12})$polycarboxylic acid.

A third aspect of the invention relates to a process for the preparation of the food-grade coated particle as defined above, which comprises:

a') spraying a solution of a alkali metal hydroxide onto a $(C_4$-$C_{12})$polycarboxylic acid to form a layer of an alkali metal salt of a $(C_4$-$C_{12})$polycarboxylic acid (i) as defined above; and b') spraying a film-forming agent (ii) onto the particles of step a) until the weight ratio between (i) and (ii) is from 20:80 to 40:60.

The particles of the invention as defined above may be used for preparing foodstuffs. Thus, further aspects of the invention relate to the use of the food-grade coated particles as food additives, and to foodstuffs comprising the food-grade coated particles optionally together with further edible components.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply throughout the description and claims.

Unless otherwise stated, all percentages mentioned herein regarding the components of the composition are expressed in weight, with respect to the total weight of the particles or the coating, provided that the sum of the amounts of the components is equal to 100%.

For the purposes of the invention, the term "about" or "around" refers to a range of values ±10% of a specified value. For example, the expression "about 20" or "around 20" includes ±10% of 20, i.e. from 18 to 22.

For the purposes of the invention, room temperature refers to 20-25° C.

The term "food grade" is used herein means either fit for human or animal consumption, or at least permitted to come into contact with food. The term "edible," as used herein, means non-toxic and suitable for consumption.

The particles of the invention are in the form of a core-shell microencapsulate, i.e., they comprise a core and a coating. For the purposes of the invention, the terms "encapsulated" and "coated" are used interchangeably and refer to the fact that the core comprising the $(C_4$-$C_{12})$polycarboxylic acid is fully surrounded with the coating.

The terms "coating" and "shell" are used herein interchangeably and refer to a layer covering the core. The term "single-component" coating or shell refers herein to the fact that the coating or shell contains only one of the alkali metal salt of the $(C_4$-$C_{12})$polycarboxylic acid or the film-forming agent. The term "combined-" coating or shell refers herein to the fact that the coating or shell contains a combination of both, the alkali metal salt of the $(C_4$-$C_{12})$polycarboxylic acid and the film-forming agent.

In one particular embodiment of the invention, optionally in combination with one or more features of the various embodiments described above or below, the invention relates to a food-grade particle, which consists of a core and a single coating layer (i.e. the core is surrounded by only one coating layer), wherein the composition of the core and of the coating layer is as defined herein.

In another particular embodiment of the invention, optionally in combination with one or more features of the various embodiments described above or below, the particles of the invention are substantially rounded.

Generally, the particles of the invention have a mean particle size from 100 to 1000 μm, more particularly from 300 to 700 μm, depending on the application in which they are used. The mean particle size as used herein corresponds to the D50 (also referred to as Dv(50)), which is the point in the size distribution, up to and including which, 50% of the total volume of material in the sample is contained. The mean particle size can be measured by means of a vibrational sieve (FTL-0200, from FILTRA).

In another particular embodiment of the invention, optionally in combination with one or more features of the various embodiments described above or below, the particles of the invention have a mean particle size from 100 to 1000 μm, more particularly, from 200 to 800 μm, even more particularly from 300 to 600 μm.

In the particles of the invention, the core comprises a $(C_4$-$C_{12})$polycarboxylic acid, and the coating comprises an alkali metal salt of a $(C_4$-$C_{12})$polycarboxylic acid. The polycarboxylic acid of the core and the polycarboxylic acid in the form of a salt present in the coating may be the same or different.

For the purposes of the invention, the term "$(C_4$-$C_{12})$ polycarboxylic acid" refers to an acyclic or cyclic polycarboxylic acid containing from 4 to 12 carbon atoms and more than one carboxylic acid group. The polycarboxylic acids may be saturated or unsaturated. Examples of $(C_4$-$C_{12})$ polycarboxylic acids include, without limitation, succinic acid, itaconic acid, maleic acid, fumaric acid, citric acid, oxalic acid, malic acid, adipic acid, tartaric acid, and the like.

The term "alkali metal salt of a $(C_4$-$C_{12})$polycarboxylic acid" refers to an alkali metal salt of a $(C_4$-$C_{12})$polycarboxylic acid as defined above, wherein at least one carboxylic group is in the acid form, and at least one carboxylic group is in the salt form. Examples of alkali metal salts include, without limitation, sodium, potassium, calcium, and combinations thereof.

In one particular embodiment of the invention, optionally in combination with one or more features of the various embodiments described above or below, the core comprises a $(C_4$-$C_{12})$polycarboxylic acid selected from the group consisting of succinic acid, itaconic acid, maleic acid, oxalic acid, malic acid, citric acid, fumaric acid, tartaric acid, adipic acid, and a combination thereof; more particularly, selected from the group consisting of malic acid, citric acid, fumaric acid, tartaric acid, adipic acid, and a combination thereof; even more particularly the $(C_4$-$C_{12})$polycarboxylic acid comprised in the core is malic acid.

In another particular embodiment of the invention, optionally in combination with one or more features of the various embodiments described above or below, the coating comprises an alkali metal salt of a $(C_4$-$C_{12})$polycarboxylic acid selected from the group consisting of sodium or potassium monohydrogen malate, sodium or potassium dihydrogen citrate, disodium or dipotassium monohydrogen citrate, and combinations thereof. Even more particularly, the coating comprises an alkali metal salt of a $(C_4$-$C_{12})$polycarboxylic acid selected from the group consisting of sodium or potassium monohydrogen malate.

In another particular embodiment of the invention, optionally in combination with one or more features of the various embodiments described above or below, the polycarboxylic acid of the core and the polycarboxylic acid in the form of a salt present in the coating are the same.

As mentioned above, the weight ratio in the coating between the alkali metal salt of the $(C_4$-$C_{12})$polycarboxylic acid (i) and the film-forming agent (ii) is from 20:80 to 40:60. In one particular embodiment of the invention, optionally in combination with one or more features of the various embodiments described above or below, the weight ratio in the coating between (i) and (ii) is from 25:75 to 35:65. In another embodiment, the weight ratio in the coating between (i) and (ii) is 20:80, or 25:75, or 30:70, or 35:65, or 40:60.

In another particular embodiment of the invention, optionally in combination with one or more features of the various embodiments described above or below, the coating consists of (i) an alkali metal salt of a ($C_4$-$C_{12}$)polycarboxylic acid, and (ii) a film-forming agent. In a more particular embodiment, (i) and (ii) are present in the coating in an amount from 20% to 40% and from 60 to 80%, by weight with respect to the total coating weight, respectively, so that the sum of the weight % of (i) and (ii) is 100%. In another more particular embodiment, (i) and (ii) are present in the coating in an amount from 25% to 35% and from 65 to 75%, by weight with respect to the total coating weight, respectively, so that the sum of the weight % of (i) and (ii) is the 100% of the coating. In another more particular embodiment, the alkali metal salt of the ($C_4$-$C_{12}$)polycarboxylic acid and the film-forming agent are present in the coating in an amount of 20% and 80%, or 25% and 75%, or 30% and 70%, or 35% and 65%, or 40% and 60%, by weight with respect to the total coating weight, respectively.

The coating of the particles of the invention further comprises a film-forming agent. A film-forming coating agent is designed to form a continuous and homogeneous protecting film over a surface. The main goal of the film-forming agent is to aisle or protects the inner particle from the outer environment or to delay the physical or chemical action that the particle should do until it is released, which take part in a determined conditions where the coating agent is dissolved or melted.

A coating agent with film-forming capacity should be capable to generate a homogeneous and continuous solid layer when the coating is cooled or dried over a surface without individual crystal presence. Also, it should be capable to reduce or delay in time at least 50% of interactions with the environment (like dissolution, hygroscopicity, oxidation . . . ) with very few quantity of coating agent.

Typical film forming agents included a liquid/molten coating material, or a solution of coating material in liquid, preferable water, which becomes volatilized during the coating process.

In one particular embodiment of the invention, optionally in combination with one or more features of the various embodiments described above or below, the film-forming agent has emulsifying properties.

In one particular embodiment of the invention, optionally in combination with one or more features of the various embodiments described above or below, the film-forming agent is selected from the group consisting of glycerides, polyglyceryl ($C_4$-$C_{28}$)fatty esters, sorbitan ($C_4$-$C_{28}$)fatty esters, cellulose ethers, including water-soluble cellulose compounds (e.g. hydroxypropylmethylcellulose, hydroxymethylcellulose), polysaccharides (e.g. maltodextrin), polyols (e.g. maltitol, sorbitol), natural gums (e.g. Arabic gum, acacia gum), modified starches, proteins (e.g. casein, gelatin), alkali metal salts of ($C_4$-$C_{12}$)polycarboxylic acids (e.g. citric acid, malic acid, sorbic acid, ascorbic acid), alkali metal salts of phosphoric acid, and combinations thereof.

Glycerides or acylglycerols are esters formed from glycerol and ($C_4$-$C_{28}$)fatty acids and can be produced biologically or industrially. For the purposes of the present invention, the term "($C_4$-$C_{28}$)fatty acid" refers to a carboxylic acid with a long aliphatic chain, which is either liner or branched, saturated or unsaturated, and contains from 4 to 28 carbon atoms. Examples of fatty acids include, without limitation, stearic acid, cerotic acid, isostearic acid, palmitic acid, oleic acid, linoleic acid, myristic acid, behenic acid, arachidic acid, montanic acid, capric acid, lauric acid, and combinations thereof.

Depending on the number of the hydroxyl functional groups of the glycerol that are esterified, glycerides are classified as monoglycerides (one hydroxyl functional group esterified with one fatty acid molecule), diglycerides (two hydroxyl functional groups esterified with two fatty acid molecules), and triglycerides (three hydroxyl functional group esterified with three fatty acid molecules).

As glycerol contains both primary and secondary alcohol groups, different types of monoglycerides and diglycerides may be formed. Monoglycerides can be 1-monoacylglycerols where the fatty acid is attached to a primary alcohol, or 2-monoacylglycerols where the fatty acid is attached to the secondary alcohol. Diglycerides can be 1,2-diacylglycerols where the fatty acids are attached to the secondary and one of the primary alcohols, or 1,3-diacylglycerols where the fatty acid are attached to the primary alcohols.

Polyglyceryl ($C_4$-$C_{28}$)fatty esters are mixed partial esters formed by reacting polymerized glycerols with edible fats, oils, or fatty acids, wherein the fatty acids are as previously defined. Polyglyceryl ($C_4$-$C_{28}$)fatty esters can have the formula:

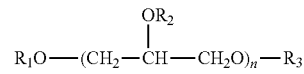

where the average value of n from 2 to 20 and each of R1, R2 and R3 are independently a fatty acid moiety or hydrogen. Examples of polyglyceryl ($C_4$-$C_{28}$)fatty esters include, without limitation, hexaglyceryl myristate, decaglyceryl myristate, hexaglyceryl oleate, decaglyceryl oleate, hexaglyceryl laurate, decaglyceryl laurate, decaglyceryl stearate and the like.

Sorbitan ($C_4$-$C_{28}$)fatty esters (also known as Spans) are esters of sorbitan with fatty acids, wherein the fatty acids are as previously defined. Examples of sorbitan ($C_4$-$C_{28}$)fatty esters include, without limitation, sorbitan monolaurate, sorbitan monostearate, sorbitan monooleate, sorbitan monopalmitate and the like.

Polysaccharides are polymers comprising a backbone consisting basically of monosaccharide repeating units and/or derivatized monosaccharide repeating units. Polymers can be composed by long linear chains to highly branched ones. Examples of polysaccharides include, without limitation, starches, modified starches, amylopectin, modified amylopectin, amylose, modified amylose, chitosan, chitin, guar gum, maltodextrin, modified guar gum, locust bean gum, cellulose (long linear polymer of D-glucose), modified cellulose such as carboxyalkylated cellulose and carboxymethyl cellulose, oxidized polysaccharides, sulfated polysaccharides, cationic polysaccharides, pectin, arabic gum, karaya gum, xanthan, carrageenans, agar-agar and alginates. Polysaccharides are capable to form structural films. Depending of their structure, the polysaccharides can be soluble or insoluble in water.

In one particular embodiment of the invention, optionally in combination with one or more features of the various embodiments described above or below, the film-forming agent is selected from the group consisting of glycerides, polyglyceryl ($C_4$-$C_{28}$)fatty esters, sorbitan ($C_4$-$C_{28}$)fatty esters, polysaccharides, and combinations thereof. More particularly, the film-forming agent is selected from the group consisting of monoglycerides, diglycerides, polyglyceryl ($C_4$-$C_{28}$)fatty esters, sorbitan ($C_4$-$C_{28}$)fatty esters, polysaccharides, and combinations thereof.

In one particular embodiment of the invention, optionally in combination with one or more features of the various embodiments described above or below, the glycerides are selected from the group consisting of glycerides of stearic acid, cerotic acid, isostearic acid, palmitic acid, oleic acid, linoleic acid, myristic acid, behenic acid, arachidic acid, montanic acid, capric acid, lauric acid, and combinations thereof. More particularly, the glycerides are selected from the group consisting of monoglycerides, diglycerides, and combinations thereof. Even more particularly, the glycerides are monoglycerides and even more particularly, the monoglycerides are 1-monoacylglycerols. In one particular embodiment of the invention, optionally in combination with one or more features of the various embodiments described above or below, the glyceride is glycerol monostearate (2,3-dihydroxypropyl octadecanoate). In another particular embodiment of the invention, optionally in combination with one or more features of the various embodiments described above or below, the glyceride is glycerol distearate, more particularly, (2-hydroxy-3-octadecanoyloxypropyl) octadecanoate or (3-hydroxy-2-octadecanoyloxypropyl) octadecanoate.

In one particular embodiment of the invention, optionally in combination with one or more features of the various embodiments described above or below, the coating is present in the particle in an amount from 10 to 40% by weight with respect to the total particle weight. In a more particular embodiment, optionally in combination with one or more features of the various embodiments described above or below, the coating is present in the particle in an amount from 10 to 30%, more particularly from 15 to 25%, by weight with respect to the total particle weight.

As previously mentioned, the invention also refers to processes for the preparation of the food-grade particles as defined above. There are several forms to obtain the combined-shell: (i) dispersion or dissolution of the alkali metal salt of the polycarboxylic acid into the film-forming agent; (ii) emulsion of the alkali metal salt of the polycarboxylic acid solution into the film-forming agent; or (iii) generation of the alkali metal salt of the polycarboxylic acid by in situ neutralization of the core surface followed by the spraying the film-forming agent to fill up the holes.

Typically, the coating medium employed may be a liquid/molten coating material, or a solution of coating material in liquid, preferable water, which becomes volatilized during the coating process.

Thus, it forms part of the invention a process for the preparation of the food-grade coated particles as defined above, which comprises:
a) dispersing or dissolving an alkali metal salt of a ($C_4$-$C_{12}$) polycarboxylic acid (i) wherein at least one carboxylic group of the ($C_4$-$C_{12}$)polycarboxylic acid is in the acid form, and at least one carboxylic group of the ($C_4$-$C_{12}$)polycarboxylic acid is in the salt form, in a film-forming agent (ii) at a suitable temperature; wherein the weight ratio between (i) and (ii) is from 20:80 to 40:60; and
b) spraying the dispersion or solution of step a) onto a ($C_4$-$C_{12}$)polycarboxylic acid.

In one particular embodiment, optionally in combination with one or more features of the various embodiments described above or below, step a) is carried out at a temperature from 30 to 100° C., more particularly from 30 to 60° C.

In another particular embodiment, optionally in combination with one or more features of the various embodiments described above or below, in step a) the alkali metal salt of the ($C_4$-$C_{12}$)polycarboxylic acid is dispersed in a previously melted film-forming agent.

In an alternative particular embodiment, optionally in combination with one or more features of the various embodiments described above or below, in step a) the alkali metal salt of the ($C_4$-$C_{12}$)polycarboxylic acid is in the form of an aqueous solution and is emulsified with a previously melted film-forming agent. Typically, the more concentrated solution achieved, the better for the time-processing.

In another particular embodiment, optionally in combination with one or more features of the various embodiments described above or below, step b) is carried out at a temperature from 30-60° C., more particularly from 35 to 50° C.

In another particular embodiment, optionally in combination with one or more features of the various embodiments described above or below, step b) is carried out at a flow rate of 5-20 g/min per Kg of final product.

In another particular embodiment, optionally in combination with one or more features of the various embodiments described above or below, step b) is carried out under a spray pressure from 1.0 to 3.5 bar, more particularly from 1.5 to 3.5 bar, and even more particularly from 2 to 3 bar.

The present invention also relates to a process for the preparation of the food-grade coated particle as defined above, which comprises:
a') spraying a solution of a alkali metal hydroxide onto a ($C_4$-$C_{12}$)polycarboxylic acid to form a layer of an alkali metal salt of a ($C_4$-$C_{12}$)polycarboxylic acid (i) wherein at least one carboxylic group of the ($C_4$-$C_{12}$)polycarboxylic acid is in the acid form, and at least one carboxylic group of the ($C_4$-$C_{12}$)polycarboxylic acid is in the salt form; and
b') spraying a film-forming agent (ii) onto the particles of step a') until the weight ratio between (i) and (ii) is from 20:80 to 40:60.

In one particular embodiment, optionally in combination with one or more features of the various embodiments described above or below, step a) is carried out at a temperature from 30 to 100° C., more particularly from 30 to 60° C.

In another particular embodiment, optionally in combination with one or more features of the various embodiments described above or below, step a) is carried out at a flow rate of 5-20 g/min per Kg of final product.

In another particular embodiment, optionally in combination with one or more features of the various embodiments described above or below, step a) is carried out under a spray pressure 1.0 to 3.5 bar, more particularly from 1.5 to 3.5 bar, and even more particularly from 2 to 3 bar.

In another particular embodiment, optionally in combination with one or more features of the various embodiments described above or below, step b) is carried out at a temperature from 30-60° C., more particularly from 35 to 50° C.

In another particular embodiment, optionally in combination with one or more features of the various embodiments described above or below, in step b') the film-forming agent is previously melted before spraying.

In another particular embodiment, optionally in combination with one or more features of the various embodiments described above or below, step b) is carried out at a flow rate of 5-20 g/min per Kg of final product.

In another particular embodiment, optionally in combination with one or more features of the various embodiments described above or below, step b) is carried out under a spray pressure 1.0 to 3.5 bar, more particularly from 1.5 to 3.5 bar and even more particularly from 2 to 3 bar.

The particular embodiments mentioned above in connection with the particles of the invention also apply to the product-by-process embodiments.

The invention also relates to a food-grade coated particle comprising:
a) a core that comprises a ($C_4$-$C_{12}$)polycarboxylic acid; and
b) a coating that comprises:
  (i) an alkali metal salt of a ($C_4$-$C_{12}$)polycarboxylic acid wherein at least one carboxylic group of the ($C_4$-$C_{12}$)polycarboxylic acid is in the acid form, and at least one carboxylic group of the ($C_4$-$C_{12}$)polycarboxylic acid is in the salt form, and
  (ii) a film-forming agent; wherein
  the weight ratio between (i) and (ii) is from 20:80 to 40:60.
obtainable by a method comprising the steps of:
a) dispersing or dissolving an alkali metal salt of a ($C_4$-$C_{12}$) polycarboxylic acid (i) wherein at least one carboxylic group of the ($C_4$-$C_{12}$)polycarboxylic acid is in the acid form, and at least one carboxylic group of the ($C_4$-$C_{12}$)polycarboxylic acid is in the salt form, in a film-forming agent (ii) at a suitable temperature; wherein the weight ratio between (i) and (ii) is from 20:80 to 40:60; and
b) spraying the dispersion or solution of step a) onto a ($C_4$-$C_{12}$)polycarboxylic acid.

The invention also relates to a food-grade coated particle comprising:
a) a core that comprises a ($C_4$-$C_{12}$)polycarboxylic acid; and
b) a coating that comprises:
  (i) an alkali metal salt of a ($C_4$-$C_{12}$)polycarboxylic acid wherein at least one carboxylic group of the ($C_4$-$C_{12}$)polycarboxylic acid is in the acid form, and at least one carboxylic group of the ($C_4$-$C_{12}$)polycarboxylic acid is in the salt form, and
  (ii) a film-forming agent; wherein
  the weight ratio between (i) and (ii) is from 20:80 to 40:60.
obtainable by a method comprising the steps of:
a') spraying a solution of a alkali metal hydroxide onto a ($C_4$-$C_{12}$)polycarboxylic acid to form a layer of an alkali metal salt of a ($C_4$-$C_{12}$)polycarboxylic acid (i) wherein at least one carboxylic group of the ($C_4$-$C_{12}$)polycarboxylic acid is in the acid form, and at least one carboxylic group of the ($C_4$-$C_{12}$)polycarboxylic acid is in the salt form; and
b') spraying a film-forming agent (ii) onto the particles of step a) until the weight ratio between (i) and (ii) is from 20:80 to 40:60.

The particular embodiments mentioned above in connection with the processes of preparation of the particles and with the particles themselves also apply to the product-by-process embodiments.

The expression food-grade coated particle "obtainable by the process" of the invention is used herein for defining the food-grade coated particle by its preparation process and refers to the composition that can be obtained through the preparation process which comprises the steps a) and b), or i) to iii), or a) and b) as previously defined. For the purposes of the invention, the expressions "obtainable", "obtained" and similar equivalent expressions are used interchangeably and, in any case, the expression "obtainable" encompasses the expression "obtained".

The particles of the invention can be used in the preparation of different foodstuffs. Thus, the present invention also relates to the use of the food-grade coated particles as defined above as a food additives, and to foodstuffs comprising the food-grade coated particles as defined above optionally together with further edible components.

In one particular embodiment, optionally in combination with one or more features of the various embodiments described above or below, the foodstuff is a confectionary product, more particularly a hard or soft candy or a chewing gum.

The particles of the invention can be also used in the preparation of feed products, cosmetic products and pharmaceutical products. Thus, the present invention also relates to feed products, cosmetic products and pharmaceutical products comprising the food-grade coated particles as defined above.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention.

The following examples are provided by way of illustration, and they are not intended to be limiting of the present invention. Furthermore, the present invention covers all possible combinations of particular and preferred embodiments described herein.

EXAMPLES

Example 1—Malic Acid Coated by a Combined-Shell Comprising Sodium Monohydrogen Malate Dispersed into Melted Monoglycerides A granulator/mixer/fluid bed device equipped with a spray nozzle was used. Initially, malic acid (800 g) was used as a core, added to the equipment and fluidized by dry air at controlled temperature from 30 to 60° C., preferably between 40-50° C. In this example, the edible film-former used was a mixture of alkali metal salt of a polycarboxylic acid dispersed at 20-40% w/w in the melted monoglycerides. In particular, sodium monohydrogen malate (60 g) was finely dispersed by a mixer into the melted monoglycerides of stearic acid (140 g) (2,3-dihydroxypropyl octadecanoate, VEROL N90) being pre-heated above the melting point (100° C.). The heated dispersion (200 g) was sprayed over the core maintaining the product temperature from 30 to 60° C., preferably between 40-50° C. The flow rate of the pump was between 5-10 g/min and the spray pressure was 3 bar. This edible film-forming coating was completed after 30 minutes. The particles obtained contained a light coating in an amount around 20% weight of the total compound weight. The coating (combined-shell) contained about 30% weight of sodium monohydrogen malate and about 70% weight of monoglycerides of stearic acid.

The particle size profile of the resulting encapsulated malic acid was determined by means of a vibrational sieve (FTL-0200, from Filtra). Most part of the particles, around 80-85%, presented a size of 300-425 μm.

Example 2—Malic Acid Coated by a Combined-Shell Comprising Sodium Monohydrogen Malate Emulsified into Melted Monoglycerides The procedure of Example 1 was repeated with the difference that the combined-shell was generated by means of an emulsion between the melted monoglycerides and the aqueous solution of the alkali metal salt of the polycarboxylic acid. Conditions to generate the combined-shell were quite different from example 1. Here the salt (sodium monohydrogen malate) was previously dissolved in water or obtained by in situ neutralization of malic acid (48 g) with a sodium hydroxide solution at 32% w/w (45 g) in distilled water (47 g). The hot aqueous solution containing 40-44% of sodium monohydrogen malate (140 g) was emulsified into melted monoglycerides of stearic acid (2,3-dihydroxypropyl octadecanoate, VEROL N90) (140 g) using a high shear mixer at a temperature around 90° C. The emulsified solution was sprayed over the core maintaining the product temperature from 30 to 60° C., preferably between 40-50° C. The flow rate of the pump was between 5-10 g/min and the spray pressure was 3 bar. This edible film-forming coating was completed after 30 minutes. The particles obtained contained a light coating in an amount around 20% weight of the total compound weight. The coating (combined-shell) contained about 30% weight of sodium monohydrogen malate and about 70% weight of monoglycerides of stearic acid.

The particle size profile of the resulting encapsulated malic acid was determined by means of a vibrational sieve (FTL-0200, from Filtra). Most part of the particles, around 80-85%, presented a size of 300-425 μm.

Example 3—Malic Acid Coated by a Combined-Shell Comprising Sodium Monohydrogen Malate (Generated In Situ) and Monoglycerides The procedure of Example 1 was repeated with the difference that the combined-shell was generated in situ. Initially, malic acid (800 g) was used as a core, added to the equipment and fluidized by dry air at controlled temperature from 30 to 60° C., preferably between 40-50° C. An aqueous solution of sodium hydroxide at 32% w/w (50 g) was sprayed over the core without being pre-heated. The flow rate of the pump was 10 g/min and the spray pressure was 3 bar. The heated inlet-air maintained the fluidization of the product with a temperature from 30 to 60° C., preferably between 40-50° C. This wetting process allowed generating in situ the malate-salt (sodium hydrogen malate) coating part over the core after 5 minutes achieving a salt percentage of about 7%. Following this, glycerides were sprayed in the following conditions to create the combined-shell protection: Monoglycerides of stearic acid (2,3-dihydroxypropyl octadecanoate, VEROL N90) (130 g) were heated above the melting point (100° C.). The melted solution was sprayed over the core maintaining the product temperature from 30 to 60° C., preferably between 40-50° C. The flow rate of the pump was between 5-10 g/min and the spray pressure was 3 bar. This edible film-forming coating was completed after 20 minutes. The particles obtained contained a light coating in an amount around 20% weight of the total compound weight. The coating (combined-shell) contained about 7% weight of sodium monohydrogen malate and about 13% weight of monoglycerides of stearic acid.

The particle size profile of the resulting encapsulated malic acid was determined by means of a vibrational sieve (FTL-0200, from Filtra). Most part of the particles, around 80-85%, presented a size of 300-425 μm.

Comparative Example 4—Malic Acid Coated by a Single-Component Shell Comprising Monoglycerides The procedure of Example 1 was repeated with the difference that the coating was only formed from the emulsifier film-former (single-component shell). In this case, monoglycerides of stearic acid (2,3-dihydroxypropyl octadecanoate, VEROL N90) (200 g) were heated above the melting point (100° C.). The melted solution was sprayed over the core of malic acid (800 g), previously added to the equipment and fluidized by dry air at controlled temperature from 30 to 60° C., preferably between 40-50° C. During spraying the product temperature was maintained from 30 to 60° C., preferably between 40-50° C. The flow rate of the pump was between 5-10 g/min and the spray pressure was 3 bar. This edible film-forming coating was completed after 20 minutes. The coating (single-component shell) was present in an amount around 20% weight with respect of the total particle weight.

The particle size profile of the resulting encapsulated malic acid was determined by means of a vibrational sieve (FTL-0200, from Filtra). Most part of the particles, around 80-85%, presented a size of 300-425 μm.

Comparative Example 5—Malic Acid Coated by a Single-Component Shell Comprising Sodium Monohydrogen Malate The procedure of Example 1 was repeated with the difference that the coating was only formed from the alkali metal salt of a polycarboxylic acids (sodium monohydrogen malate) into a fluid bed equipped with a nozzle sprayer as described in U.S. Pat. No. 8,431,171. Malic acid (500 g) was added to the fluid bed, fluidized by dry air and heated up to 60° C. A warm aqueous solution of sodium monohydrogen malate at 40% in water at 90° C. (made previously as described in example 2 by in situ neutralization of the malic acid (415 g) with alkali hydroxide solution at 32% w/w (385 g) in distilled water (400 g)) was sprayed over the core being pre-heated at 60° C. The flow rate average of the pump was 15 g/min and the spray pressure was 3 bar. The heated inlet-air maintained the fluidization of the product with a temperature around 60° C. Spraying sodium monohydrogen malate solution was stopped after 20 minutes to achieve a 315 g of solution sprayed over the malic acid. The coating (single-component shell) was present in the same amount of previous examples, around 20% weight with respect of the total particle weight.

The particle size profile of the resulting encapsulated malic acid was determined by means of a vibrational sieve (FTL-0200, from Filtra). Most part of the particles, around 80-85%, presented a size of 300-425 μm.

Comparative Example 6—Malic Acid Coated by a Single-Component Shell Comprising Sodium Monohydrogen Malate The procedure of comparative Example 5 was repeated with the difference that the coating was increased from 20% to 35% just to see differences between quantities of coating in the selected properties.

The procedure was exactly the same, only the coating time with the hot solution of sodium hydrogen malate at 40% was increased to 45 minutes to achieve a 675 g of solution sprayed over the malic acid. The coating (single-component shell) was increased to 35% in weight with respect of the total particle weight.

The particle size profile of the resulting encapsulated malic acid was determined by means of a vibrational sieve (FTL-0200, from Filtra). Most part of the particles, around 80-85%, presented a size of 300-425 μm.

Comparative Example 7—Malic Acid Coated by a Single-Component Shell Comprising Sodium Monohydrogen Malate The procedure of comparative Example 5 was repeated with the difference that the coating was increased from 20% to 50% just to see differences between quantities of coating in the selected properties.

The procedure was exactly the same, only the coating time with the hot solution of sodium hydrogen malate at 40% was increased to 80 minutes to achieve a 1200 g of solution sprayed over the malic acid. The coating (single-component shell) was increased to 50% in weight with respect of the total particle weight.

The particle size profile of the resulting encapsulated malic acid was determined by means of a vibrational sieve (FTL-0200, from Filtra). Most part of the particles, around 80-85%, presented a size of 300-425 μm.

Particle Characterization

The different pH values between salts (sodium monohydrogen malate and disodium malate) and the fully hydrogenated polycarboxylic acid form (malic acid) were used to determine the percentage of salt present in the particles of the invention (examples 1-3) as well as in the particles of the prior art (comparative examples 4-7).

The measure of the pH was performed by dissolving each tested product at 1% w/v in deionized water at 25° C. The solution was allowed to stabilize a few minutes before the pH reading (CRISON microPH 2002).

Table 1 shows the pH values of pure acid and their salts, which are named a, b and c respectively: (a) malic acid; (b) sodium monohydrogen malate; and (c) disodium malate; and the pH values obtained for the different tested particles. Lower pH values indicate a higher percentage of malic acid in front their salts and consequently less taste modification.

TABLE 1

| Examples | a | b | c | 1 | 2 | 3 | 4 (comparative) | 7 (comparative) |
|---|---|---|---|---|---|---|---|---|
| pH | 2.1 | 4.0 | 8.0 | 2.3 | 2.2 | 2.3 | 2.1 | 3.2 |

As can be seen, examples 1 to 3 show pH values where salt content is below 10% w/w of the total product. In example 4 there is no salt in the product. Finally, in example 7 where salt content is higher than the rest, pH around 3.2 is coherent to be made by the acid and the partially hydrogenated polycarboxylic acid form with a percentage around 50% of the salt.

Stability Assay

Stability of examples of the invention 1-2 as well as comparative examples 4-7 was conducted in a controlled temperature and humidity chamber. The shell's ductility against cracking was evaluated by shaking previously the samples at 40 rpm during 30 min. followed by maintaining the microencapsulated products into a controlled chamber at 85% of relative humidity (R.T.) during several days. The hygroscopic tendency was measured as a value of water entrapment. The more hygroscopic tendency is showed the less coating protection of the active will be. In this case, the less coating protection is due to the coating cracking produced during friction assay.

Table 2 shows the obtained results. Value 3 indicates water entrapped by the product after 3 days into the chamber conditions (25° C., 85% R.T.). Value 2 indicates water entrapped by the product after 7 days into the chamber conditions (25° C., 85% R.T.). Value 1 indicates water entrapped by the product after 15 days into the chamber conditions (25° C., 85% R.T.). Value 0 indicates no changes in the product after 15 days.

TABLE 2

| Examples | 1 | 2 | 3 | 4 (comparative) | 5 (comparative) | 6 (comparative) | 7 (comparative) |
|---|---|---|---|---|---|---|---|
| Hygroscopic tendency | 0 | 0 | 1 | 0 | 3 | 3 | 2 |

As indicated in table 1, the products of the invention showed null or very low hygroscopic tendency after friction, which is a measure of the brittleness of the particles and, as a consequence, a better coating protection. Further, when malic acid is coated by a single-component shell comprising monoglycerides (comparative example 4) no hygroscopic tendency was seen, but the inventors found that these particles were too soft so that they were difficult to manipulate as well.

On the other hand, when malic acid is coated by a single-component shell of sodium monohydrogen malate (comparative example 5 to 7), wherein the coating was present in an amount around 20% weight with respect of the total particle weight, the particle showed some hygroscopic tendency after 3 days. It was seen that in order to reduce the hygroscopicity of the comparative example containing a single-component shell of monohydrogen malate it was necessary to significantly increase the thickness of the coating around 50% weight with respect of the total particle weight (at 35% the same result as at 20% was observed), and even in this case the hygroscopic tendency was higher than for the particles of the invention. However, in this way the salt content should be increased until 50% to obtain a good protection and, as a consequence, the taste of the particles was modified which is undesirable.

Dynamic Vapor Sorption Isotherms

In order to evaluate and compare the hygroscopic tendency of the resulting products a Dynamic Vapor Sorption (DVS) Isotherm analysis was performed (AquaLab Vapor Sorption Analyzer (VSA). This analysis allows determining the water activity and the weight change of the samples at different conditions of relative humidity at a constant temperature. The results of the DVS analysis are shown in the table 3.

TABLE 3

| % change in mass (by dry weight at 25° C.) | | | | |
|---|---|---|---|---|
| R. H. (%) | Malic acid | Example 1 | Example 2 | Example 3 |
| 0 | 0.0 | 0.0 | 0.0 | 0.0 |
| 15 | 0.0 | 0.0 | 0.0 | 0.0 |
| 35 | 0.1 | 0.0 | 0.0 | 0.0 |
| 65 | 0.3 | 0.8 | 0.7 | 0.6 |
| 85 | 60.3 | 32.5 | 33.1 | 29.7 |

It was shown that when the R.H. was increased, the particles of the invention showed a significant lower vapour pressure (and therefore lower hygroscopic tendency) than malic acid without coating. Thus, the particles of the invention show good shelf life and hygroscopic protection.

Migration of Malic Acid into Soft Candies (Gelatin Based Gels)

In order to evaluate the degree of encapsulation of malic acid in the particles of the invention, a migration assay of malic acid into soft candies (gelatin based gels) was performed.

600 g gel masses containing 35% (w/w) gelatin 250 bloom in water were prepared at 80° C. In parallel a mixture of sugar, glucose syrup and water was prepared at 116° C. and cooled at 80° C. Afterwards, both dissolutions were mixed and methyl red indicator was added to the solution. The final mixture was distributed into glass tubes and left to solidify for 24 hours. The same amount of malic acid from each sample (pure malic acid and encapsulated malic acid particles of examples 1-3 of the invention) was scattered on top of the gelatin tubes and incubated at room temperature (25° C.) and at 37° C. during 10 and 20 days. The migration of malic acid was evaluated visually and the distance of the migration front from the top of the gelatin was measured at days 10, 15 and 20 for the tubes kept at 25° C., and at day 5 and 10 for the tubes kept at 37° C. The results of the migration assay are shown below:

TABLE 4

| ACID MALIC MIGRATION (mm) | | | | |
|---|---|---|---|---|
| | Malic acid | Example 1 | Example 2 | Example 3 |
| 25° C. | | | | |
| Day 10 | 3 | 1 | 2 | 1 |
| Day 15 | 10 | 5 | 7 | 4 |
| Day 20 | 20 | 7 | 11 | 6 |
| 37° C. | | | | |
| Day 5 | 7 | 5 | 6 | 3 |
| Day 10 | 15 | 8 | 9 | 7 |

A higher migration of the pure malic acid onto the gelatin matrix was observed at both temperatures and times in comparison to the coated malic acid samples. In these samples an ascendant migration of water from the gel to the solid product over time was also observed as well as a darkening of the color, which is indicative of a higher malic acid concentration and a lower pH. Thus, the particles of the invention show good shelf life and hygroscopic protection of the encapsulated malic acid with a lower percentage of coating and a lower content of salt, maintaining a controlled migration of the coated particle into the gel.

CITATION LIST

EP3127434
U.S. Pat. No. 8,431,171

The invention claimed is:
1. A food-grade coated particle comprising:
   a) a core that comprises a ($C_4$-$C_{12}$)polycarboxylic acid; and
   b) a coating that comprises:
      (i) an alkali metal salt of a ($C_4$-$C_{12}$)polycarboxylic acid wherein at least one carboxylic group of the ($C_4$-$C_{12}$)polycarboxylic acid is in the acid form, and at least one carboxylic group of the ($C_4$-$C_{12}$)polycarboxylic acid is in the salt form, and
      (ii) a film-forming agent; wherein
   the weight ratio between (i) and (ii) is from 20:80 to 40:60.

2. The food-grade particle according to claim 1, wherein the ($C_4$-$C_{12}$)polycarboxylic acid of the core is selected from the group consisting of malic acid, citric acid, fumaric acid, tartaric acid, adipic acid and combinations thereof.

3. The food-grade particle according to claim 1, wherein the alkali metal salt of the ($C_4$-$C_{12}$)polycarboxylic acid of the coating is selected from the group consisting of sodium or potassium monohydrogen malate, sodium or potassium dihydrogen citrate, disodium or dipotassium monohydrogen citrate, and combinations thereof.

4. The food-grade particle according to claim 1, wherein the film-forming agent is selected from the group consisting of glycerides, polyglyceryl ($C_4$-$C_{28}$)fatty esters, sorbitan ($C_4$-$C_{28}$)fatty esters, cellulose ethers, polysaccharides, polyols, natural gums, modified starches, proteins, and combinations thereof.

5. The food-grade particle according to claim 4, wherein the film-forming agent is a monoglyceride.

6. The food-grade particle according to claim 1, wherein the coating is present in an amount from 10 to 40% by weight with respect to the total particle weight.

7. The food-grade particle according to claim 1, wherein the coating consists of from 20% to 40% of the alkali metal salt of the ($C_4$-$C_{12}$)polycarboxylic acid and from 60 to 80% of the film-forming agent, wherein the % are expressed by weight with respect to the total coating weight, provided that the sum of the amounts of the components is equal to 100%.

8. A process for the preparation of the food-grade coated particle as defined in claim 1, which comprises:
   a) dispersing or dissolving an alkali metal salt of a ($C_4$-$C_{12}$)polycarboxylic acid (i) wherein at least one carboxylic group of the ($C_4$-$C_{12}$)polycarboxylic acid is in the acid form, and at least one carboxylic group of the ($C_4$-$C_{12}$)polycarboxylic acid is in the salt form, in a film-forming agent (ii) at a suitable temperature; wherein the weight ratio between (i) and (ii) is from 20:80 to 40:60; and
   b) spraying the dispersion or solution of step a) onto a ($C_4$-$C_{12}$)polycarboxylic acid.

9. The process according to claim 8 wherein in step a) the alkali metal salt of the ($C_4$-$C_{12}$)polycarboxylic acid is dispersed in a previously melted film-forming agent.

10. The process according to claim 8 wherein in step a) the alkali metal salt of the ($C_4$-$C_{12}$)polycarboxylic acid is in the form of an aqueous solution and is emulsified with a previously melted film-forming agent.

11. A process for the preparation of the food-grade coated particle as defined in claim 1, which comprises:
   a') spraying a solution of a alkali metal hydroxide onto a ($C_4$-$C_{12}$)polycarboxylic acid to form a layer of an alkali metal salt of a ($C_4$-$C_{12}$)polycarboxylic acid (i) wherein at least one carboxylic group of the ($C_4$-$C_{12}$)polycarboxylic acid is in the acid form, and at least one carboxylic group of the ($C_4$-$C_{12}$)polycarboxylic acid is in the salt form; and
   b') spraying a film-forming agent (ii) onto the particles of step a') until the weight ratio between (i) and (ii) is from 20:80 to 40:60.

12. The process according to claim 11 wherein in step b') the film-forming agent is previously melted before spraying.

13. A method of using the food-grade coated particle as defined in claim 1 as a food additive, the method comprising adding the food-grade coated particle to a foodstuff or a feed product.

14. A foodstuff, a feed product, a cosmetic product or a pharmaceutical product comprising the food-grade coated particle as defined in claim 1.

15. The foodstuff according to claim 14, which is a hard or soft candy or a chewing gum.

16. The food-grade particle according to claim 2, wherein the alkali metal salt of the $(C_4-C_{12})$polycarboxylic acid of the coating is selected from the group consisting of sodium or potassium monohydrogen malate, sodium or potassium dihydrogen citrate, disodium or dipotassium monohydrogen citrate, and combinations thereof.

17. The food-grade particle according to claim 16, wherein the film-forming agent is selected from the group consisting of glycerides, polyglyceryl $(C_4-C_{28})$fatty esters, sorbitan $(C_4-C_{28})$fatty esters, cellulose ethers, polysaccharides, polyols, natural gums, modified starches, proteins, and combinations thereof.

18. The food-grade particle according to claim 6, wherein the coating consists of from 20% to 40% of the alkali metal salt of the $(C_4-C_{12})$polycarboxylic acid and from 60 to 80% of the film-forming agent, wherein the % are expressed by weight with respect to the total coating weight, provided that the sum of the amounts of the components is equal to 100%.

19. The food-grade particle according to claim 16, wherein the coating consists of from 20% to 40% of the alkali metal salt of the $(C_4-C_{12})$polycarboxylic acid and from 60 to 80% of the film-forming agent, wherein the % are expressed by weight with respect to the total coating weight, provided that the sum of the amounts of the components is equal to 100%.

20. The food-grade particle according to claim 17, wherein the coating consists of from 20% to 40% of the alkali metal salt of the $(C_4-C_{12})$polycarboxylic acid and from 60 to 80% of the film-forming agent, wherein the % are expressed by weight with respect to the total coating weight, provided that the sum of the amounts of the components is equal to 100%.

* * * * *